US009308051B2

(12) United States Patent
Adams et al.

(10) Patent No.: US 9,308,051 B2
(45) Date of Patent: Apr. 12, 2016

(54) ILLUMINATED TUBING SET

(75) Inventors: Grant Adams, Coon Rapids, MN (US);
Eric Wilkowske, North Oaks, MN (US)

(73) Assignee: SMITHS MEDICAL ASD, INC.,
Rockland, MA (US)

( * ) Notice: Subject to any disclaimer, the term of this patent is extended or adjusted under 35 U.S.C. 154(b) by 1079 days.

(21) Appl. No.: 13/296,883

(22) Filed: Nov. 15, 2011

(65) Prior Publication Data

US 2013/0123579 A1 May 16, 2013

(51) Int. Cl.
| | |
|---|---|
| *A61B 1/07* | (2006.01) |
| *A61B 1/12* | (2006.01) |
| *A61B 19/00* | (2006.01) |
| *A61M 39/08* | (2006.01) |
| *A61M 25/00* | (2006.01) |

(52) U.S. Cl.
CPC ............ *A61B 19/44* (2013.01); *A61M 25/0043* (2013.01); *A61M 39/08* (2013.01); *A61B 2019/444* (2013.01); *A61B 2019/464* (2013.01); *A61M 25/0026* (2013.01); *A61M 25/0045* (2013.01); *A61M 2205/276* (2013.01); *A61M 2205/6009* (2013.01); *A61M 2205/6081* (2013.01)

(58) Field of Classification Search
CPC .................. A61M 25/0043; A61M 2039/1044; A61M 39/08; A61M 25/0026; A61M 25/0045; A61M 2205/276; A61M 2205/6009; A61M 2205/081; F21K 9/30; A61B 19/44; A61B 19/444; A61B 2019/464
USPC ............... 362/84, 249.02, 551, 555, 562, 800
See application file for complete search history.

(56) References Cited

U.S. PATENT DOCUMENTS

| | | | |
|---|---|---|---|
| 2,835,252 | A | 5/1958 | Bertram |
| 2,954,028 | A | 9/1960 | Smith |

(Continued)

FOREIGN PATENT DOCUMENTS

| | | |
|---|---|---|
| CN | 2427205 Y | 4/2001 |
| EP | 2371411 A1 | 10/2011 |

(Continued)

OTHER PUBLICATIONS

Notification of Transmittal of the International Search Report and the Written Opinion of the International Searching Authority or the Declaration, Application No. PCT/US2012/065154, mailed Apr. 12, 2013, 3 pages.

(Continued)

*Primary Examiner* — Theodore Stigell
(74) *Attorney, Agent, or Firm* — Patterson Thuente Pedersen, P.A.

(57) ABSTRACT

An illuminated medical tubing set that provides visual indications of characteristics relating to the type and operating status of the tubing. An illuminated tubing set system generally comprises an optical element, a fluid conduit, and a power source. In general, the fluid conduit is used to transmit fluid in a critical care environment. The power source interfaces with the optical element. The optical element is configured to illuminate the tubing set after being powered by the power source. Optionally, the illuminated tubing set can further comprise a pressure sensor and a microcontroller. Additional sensors, such as to monitor other characteristics of the tubing, fluid, or surrounding environment, can also be included. For example, an occlusion sensor, temperature sensor, or flow sensor, or any combination thereof, can be included.

9 Claims, 6 Drawing Sheets

(56) References Cited

U.S. PATENT DOCUMENTS

| | | |
|---|---|---|
| 3,935,876 A | 2/1976 | Massie |
| 4,009,382 A | 2/1977 | Nath |
| 4,056,724 A | 11/1977 | Harte |
| 4,074,187 A | 2/1978 | Miller |
| 4,447,230 A | 5/1984 | Gula |
| 4,512,764 A | 4/1985 | Wunsch |
| 4,524,320 A | 6/1985 | Brooks |
| 4,559,036 A | 12/1985 | Wunsch |
| 4,654,026 A | 3/1987 | Underwood |
| 4,704,660 A | 11/1987 | Robbins |
| 4,782,430 A | 11/1988 | Robbins |
| 4,795,429 A | 1/1989 | Feldstein |
| 4,806,289 A | 2/1989 | Laursen |
| 4,825,341 A | 4/1989 | Awai |
| 4,830,461 A | 5/1989 | Ishiharada |
| 4,900,314 A | 2/1990 | Quackenbush |
| 4,901,922 A | 2/1990 | Kessenerg |
| 4,922,385 A | 5/1990 | Awai |
| 4,957,347 A | 9/1990 | Zarian |
| 5,016,152 A | 5/1991 | Awai |
| 5,046,456 A | 9/1991 | Heyman |
| 5,052,778 A | 10/1991 | Jamshid |
| 5,067,831 A | 11/1991 | Robbins |
| 5,118,907 A | 6/1992 | Stout |
| 5,122,580 A | 6/1992 | Zarian |
| 5,149,467 A | 9/1992 | Zarian |
| 5,190,525 A | 3/1993 | Oswald |
| 5,221,387 A | 6/1993 | Robbins |
| 5,224,932 A | 7/1993 | Lappas |
| 5,225,166 A | 7/1993 | Zarian |
| 5,298,327 A | 3/1994 | Zarian |
| 5,321,587 A | 6/1994 | Fujita |
| 5,333,227 A | 7/1994 | Ishiharada |
| 5,345,531 A | 9/1994 | Keplinger |
| 5,412,750 A | 5/1995 | Nath |
| 5,416,875 A | 5/1995 | Keplinger |
| 5,423,750 A | 6/1995 | Spiller |
| 5,425,730 A | 6/1995 | Luloh |
| 5,432,876 A | 7/1995 | Appeldorn |
| 5,463,706 A | 10/1995 | Dumont |
| 5,464,025 A | 11/1995 | Charles |
| 5,479,322 A | 12/1995 | Kacheria |
| 5,539,624 A | 7/1996 | Dougherty |
| 5,546,493 A | 8/1996 | Noguchi |
| 5,557,702 A | 9/1996 | Yoshikawa |
| 5,631,994 A | 5/1997 | Appeldorn |
| 5,638,480 A | 6/1997 | Ishiharada |
| 5,659,643 A | 8/1997 | Appeldorn |
| 5,684,913 A | 11/1997 | Sugiyama |
| 5,690,612 A | 11/1997 | Lopez |
| 5,692,088 A | 11/1997 | Ishiharada |
| 5,708,749 A | 1/1998 | Kacheria |
| 5,737,471 A | 4/1998 | Sugiyama |
| 5,779,353 A | 7/1998 | Kacheria |
| 5,788,215 A | 8/1998 | Ryan |
| 5,833,213 A | 11/1998 | Ryan |
| 5,843,045 A | 12/1998 | DuPont |
| 5,845,038 A | 12/1998 | Lundin |
| 5,873,731 A | 2/1999 | Prendergast |
| RE36,157 E | 3/1999 | Robbins |
| 5,898,810 A | 4/1999 | Devens |
| 5,903,695 A | 5/1999 | Zarian |
| 5,905,826 A | 5/1999 | Benson |
| 5,933,560 A | 8/1999 | Ishiharada |
| 5,937,127 A | 8/1999 | Zarian |
| 5,954,313 A | 9/1999 | Ryan |
| 5,974,708 A | 11/1999 | Webb et al. |
| 5,987,199 A | 11/1999 | Zarian |
| 5,995,690 A | 11/1999 | Kotz |
| 6,016,372 A | 1/2000 | Fein |
| 6,030,108 A | 2/2000 | Ishiharada |
| 6,039,553 A | 3/2000 | Lundin |
| 6,050,713 A | 4/2000 | O'Donnell |
| 6,050,715 A | 4/2000 | Hunger |
| 6,059,768 A | 5/2000 | Friedman |
| 6,123,442 A | 9/2000 | Freier |
| 6,158,458 A | 12/2000 | Ryan |
| 6,169,836 B1 | 1/2001 | Sugiyama |
| 6,198,872 B1* | 3/2001 | Lipson et al. ............... 385/117 |
| 6,215,947 B1 | 4/2001 | Abramowicz |
| 6,219,480 B1 | 4/2001 | Cassarly |
| 6,236,797 B1 | 5/2001 | Hotta |
| 6,251,311 B1 | 6/2001 | Zarian |
| 6,257,750 B1 | 7/2001 | Strasser |
| 6,267,492 B1 | 7/2001 | Reid |
| 6,272,267 B1 | 8/2001 | Hansler |
| 6,282,355 B1 | 8/2001 | Zarian |
| 6,289,150 B1 | 9/2001 | Zarian |
| 6,302,571 B1 | 10/2001 | Davenport |
| 6,304,693 B1 | 10/2001 | Buelow |
| 6,314,226 B1 | 11/2001 | Nath |
| 6,314,227 B1 | 11/2001 | Nath |
| 6,322,230 B1 | 11/2001 | Medici |
| 6,350,050 B1 | 2/2002 | Buelow |
| 6,363,197 B1 | 3/2002 | Zarian |
| 6,364,538 B1 | 4/2002 | Ishiharada |
| 6,367,941 B2 | 4/2002 | Lea |
| 6,382,824 B1 | 5/2002 | Prasad |
| 6,385,380 B1 | 5/2002 | Friedrich |
| 6,393,192 B1 | 5/2002 | Koren |
| 6,453,099 B1 | 9/2002 | Davenport |
| D465,038 S | 10/2002 | Bragg |
| 6,526,213 B1 | 2/2003 | Ilenda |
| 6,543,925 B2 | 4/2003 | Kuykendal |
| 6,545,428 B2 | 4/2003 | Davenport |
| 6,546,752 B2 | 4/2003 | Sulcs |
| 6,589,229 B1* | 7/2003 | Connelly et al. ............ 604/890.1 |
| 6,614,972 B1 | 9/2003 | Lundin |
| 6,618,530 B1 | 9/2003 | Lundin |
| 6,623,667 B2 | 9/2003 | Lundin |
| D486,263 S | 2/2004 | Grothe |
| 6,863,428 B2 | 3/2005 | Lundin |
| 6,866,427 B2 | 3/2005 | Robbins |
| 6,877,877 B2 | 4/2005 | Rodriguez |
| 6,942,373 B2 | 9/2005 | Buelow |
| D513,184 S | 12/2005 | Parker |
| 7,008,071 B2 | 3/2006 | Buelow |
| 7,029,137 B2 | 4/2006 | Lionetti |
| 7,049,937 B1 | 5/2006 | Zwieg |
| 7,052,158 B2 | 5/2006 | Rodriquez |
| 7,163,326 B2 | 1/2007 | Cassarly |
| 7,163,329 B2 | 1/2007 | Bina |
| 7,164,819 B2 | 1/2007 | Jenson |
| 7,182,484 B2 | 2/2007 | Buelow |
| 7,190,863 B2 | 3/2007 | Frankiewicz |
| 7,194,184 B2 | 3/2007 | Buelow |
| 7,198,398 B2 | 4/2007 | Buelow |
| 7,220,035 B2 | 5/2007 | Buelow |
| 7,326,188 B1 | 2/2008 | Russell |
| 7,374,318 B2* | 5/2008 | Brooks et al. ............... 362/396 |
| 7,384,165 B2 | 6/2008 | Doyle |
| 7,524,082 B2 | 4/2009 | North |
| 7,677,780 B2 | 3/2010 | Lundin |
| 7,690,331 B2 | 4/2010 | Hurwitz |
| 7,758,220 B1 | 7/2010 | Grothe |
| D621,502 S | 8/2010 | Downs |
| 7,837,069 B2 | 11/2010 | Kroub |
| 7,901,353 B2 | 3/2011 | Vayser |
| 8,373,860 B2 | 2/2013 | Kiesel |
| 2001/0016105 A1 | 8/2001 | Sugiyama |
| 2002/0054494 A1 | 5/2002 | Ishiharada |
| 2003/0004469 A1 | 1/2003 | Kraushaar |
| 2003/0152344 A1 | 8/2003 | Brunet |
| 2003/0222786 A1 | 12/2003 | Dannenmann |
| 2004/0042735 A1 | 3/2004 | Ma |
| 2004/0160774 A1 | 8/2004 | Lionetti |
| 2004/0217586 A1 | 11/2004 | Mastropaolo |
| 2004/0246700 A1 | 12/2004 | Palmer |
| 2005/0011282 A1 | 1/2005 | Voege |
| 2005/0099624 A1 | 5/2005 | Staehr |
| 2005/0171492 A1 | 8/2005 | Rodriguez |
| 2005/0182356 A1* | 8/2005 | Dixon ............................. 604/77 |
| 2005/0230575 A1 | 10/2005 | Zelenski |
| 2006/0013547 A1 | 1/2006 | Kitano |

(56) References Cited

U.S. PATENT DOCUMENTS

| | | | |
|---|---|---|---|
| 2006/0070458 A1 | 4/2006 | Jones | |
| 2006/0147161 A1 | 7/2006 | Kim | |
| 2006/0232385 A1 | 10/2006 | Scherer | |
| 2007/0103926 A1 | 5/2007 | Brooks | |
| 2007/0106263 A1 | 5/2007 | Ward | |
| 2008/0097179 A1 | 4/2008 | Russo | |
| 2008/0099313 A1 | 5/2008 | Dhir | |
| 2008/0115957 A1 | 5/2008 | Duffy | |
| 2008/0123323 A1* | 5/2008 | Brunet | 362/84 |
| 2008/0198032 A1 | 8/2008 | North | |
| 2009/0177407 A1 | 7/2009 | Lennernas | |
| 2009/0284962 A1 | 11/2009 | Grothe | |
| 2009/0310123 A1 | 12/2009 | Thomson | |
| 2010/0019755 A1 | 1/2010 | Law | |
| 2010/0231619 A1 | 9/2010 | Espinoza-Ilbarra | |
| 2011/0264045 A1 | 10/2011 | Thompson | |
| 2013/0208497 A1* | 8/2013 | Provost et al. | 362/555 |

FOREIGN PATENT DOCUMENTS

| | | |
|---|---|---|
| WO | WO 9106255 | 5/1991 |
| WO | WO 99/21600 A2 | 5/1999 |
| WO | WO 01/57435 | 8/2001 |
| WO | WO 2005/051462 | 6/2005 |
| WO | WO 2005/058410 | 6/2005 |
| WO | WO 2005/106899 | 11/2005 |
| WO | WO 2006/060688 A2 | 6/2006 |
| WO | WO 2006/065271 | 6/2006 |

OTHER PUBLICATIONS

International Report on Patentability, Application No. PCT/US2012/065154, report issued on May 20, 2014, 9 pages.
Katz, Leslie, *Bright Idea: Charging cables light up as a current flows*, www.cnet.com, © CBS Interactive, Feb. 2, 2012, 3 pages.
Dexim, *Visible Green Cable for iPad/iPhone/iPod*, © 2011, dexim, Inc., 2 pages, as available at http://dexim.net/usproducts/V~Green/DWA065.html.
Cassano-Piché, Andrea, *Multiple Line Management*, Health Technology Safety Research Team: University Health Network, Jan. 26, 2012, 31 pages.
*Projects: Mitigating Risks Associated with Multiple IV Infusions*, Centre for Global eHealth Innovation © 2013, 1 page.
Aami, *Multiple Line Management*, as available at http://www.aami.org/htsi/infusion/wg/multiple.line.html on May 15, 2013, 1 page.
European Search Report, Application No. 12848985.3, 7 pages, dated Sep. 9, 2015.
Chinese Office Action, Application No. 201280067143.3, dated Sep. 1, 2015, 7 pages.
Supplementary European Search Report, EP Application No. 12848985, completed Dec. 21, 2015. 15 pages.

* cited by examiner

ILLUMINATED TUBING SET

TECHNICAL FIELD

The invention relates generally to medical tubing, and more particularly, to illuminated medical tubing providing tubing identification.

BACKGROUND

In critical care environments, a single patient can be connected to multiple infusion pumps or other tubing-based delivery or removal systems at the same time. Because of this, a multitude of medical tubing can be near and around the patient, making it difficult for medical professionals to know which tubing relates to which infusion pump, delivery system, or removal system. Further, parameters such as route of infusion, drug interaction, and whether the line is putting fluid into the patient's body or carrying fluid away from the patient's body, for example, are critical to the care of a patient. If the wrong medication is placed in the wrong set of tubing, the results can be fatal. Thus, the organization and identification of tubing lines is vitally important.

Currently, the identification of tubing lines is done by hand, often by a medical professional hand-tracing the tubing from the infusion device, through the span of tubing, and the patient. The medical industry has devised standardized colors and patterns to indicate characteristics of medical tubing, like route of infusion and type of tube. Therefore, more updated methods of identifying tubing involves hand-labeling a tubing line with these standardized markings by adhering a label to the line after initial implementation or the tracing described above. In some instances, a single line of tubing can have multiple labels affixed to it. However, the human-executed practices described above are not only time-consuming, but also prone to mistakes in labeling or identification due to human error.

Additionally, even when the multitude of lines are labeled correctly, there remains a difficulty in reading and evaluating the labels when the room in which the patient resides is not lit. For example, when a medical professional enters a patient's darkened room, such as when the patient is sleeping at night, in order to check the connectivity or status of one or more of the lines, the professional will often have to turn the overhead room lights on, or have a supplementary light to position on the lines and labels, like a flashlight. The turning on of room lights or use of a flashlight around the patient may be disruptive to the patient's sleep. Additionally, the use of a flashlight can be cumbersome, especially when both of the professional's hands are needed for patient care. Further, some drugs are sensitive to the wavelength of certain light, thereby limiting the types of lights that may be used around medical lines.

In addition, existing medical tubing provides no indication of the operating status or, in cases of problems with the tubing or infusion, alerts for the attending medical professional. In order to check the operating status of the infusion device and attached tubing, the medical professional must first inspect the device, inspect the interface to the tubing, and subsequently trace along the tubing to evaluate a proper flow. Similarly, medical professionals are often not alerted when there is a problem with the tubing or infusion; the entire length of tubing must be visually inspected for blockages or occlusions. Thus, in addition to the problem of identifying existing medical tubing, a problem exists in identifying operating and problem statuses.

Therefore, there is a need for an automated, safe, and effective way of identifying medical tubing, as well as for identifying any operating statuses or problem statuses with the flow of the medical liquid within the tubing.

SUMMARY

Embodiments relate to illuminated medical tubing, such that individual medical lines are identifiable based on an illumination or color scheme.

In an embodiment, a medical tubing set comprises a fluid conduit adapted to convey a medical fluid, an optical element coupled to the fluid conduit and configured to provide illumination, and a power source configured to power the optical element.

In an embodiment, a method of operating a medical tubing set comprises installing the medical tubing set in a medical device at a first end and in a patient at a second end, setting at least one operating parameter of the medical tubing set, sensing at least one characteristic of the medical tubing set, comparing the at least one sensed characteristic against the at least one operating parameter, and illuminating the medical tubing set based on at least the comparison of the at least one sensed characteristic and the at least one operating parameter.

In an embodiment of a method of operating a medical tubing set, the medical tubing set comprising a fluid conduit adapted to convey a medical fluid, an optical element coupled to the fluid conduit and configured to provide illumination, and a power source configured to power the optical element, the method comprises installing the medical tubing set in a medical device at a first end and in a patient at a second end; providing a source of power with the power source; applying the source of power to the optical element; and illuminating the fluid conduit with the optical element.

The invention thereby improves the way medical tubing is identified in a critical care environment. Because the tubing provides a visual indication, no hand-tracing of tubing from the infusion device, through the span of tubing, and into the patient is required. Additionally, labels adhered to the tubing are no longer needed to identify characteristics of the tube, like route of infusion and type of tube; these characteristics can be indicated by the illumination component. Likewise, because the tubing is illuminated, the tubing is identifiable even in a darkened room, and thus no supplementary light is needed to identify individual tubes or labels. Further, sensors integrated into the tubing, like pressure sensors, occlusion sensors, fluid flow sensors, temperature sensors, liquid density sensors, air bubble sensors, salinity sensors, pH sensors, dissolved oxygen sensors, conductivity sensors, and electrolyte sensors, for example, provide data about the tubing and fluid that can be accumulated and subsequently reported as a visual indication by the illumination component. In this way, emergency situations can be instantaneously expressed by a visual indication. Manufacturing advantages also exist in embodiments. Existing medical tubing manufacturing can be modestly altered or supplemented in order to produce the tubing of the present invention. Similarly, in embodiments, existing medical devices and medical tubing can be retrofit such that the illuminated tubing of the present application is usable on devices and tubing not originally designed for it. In another advantage, various components of embodiments are highly reusable, thus lowering the cost to practitioners.

The most common source of occlusions is a clamp on the medical tubing that is previously applied to the tubing but subsequently forgotten by hospital staff. Consequently, in another advantage, when a clamp is placed on embodiments, the clamp also acts as a stimulus for the passing illumination by blocking, altering, restricting, or otherwise changing the optical path. As a result, in embodiments, the passing illumination is mostly terminated, and thereby highlighted, at the forgotten clamp. Embodiments can thus provide an obvious visual indication of forgotten clamps.

The above summary of the invention is not intended to describe each illustrated embodiment or every implementation of the present invention. The figures and the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1A:
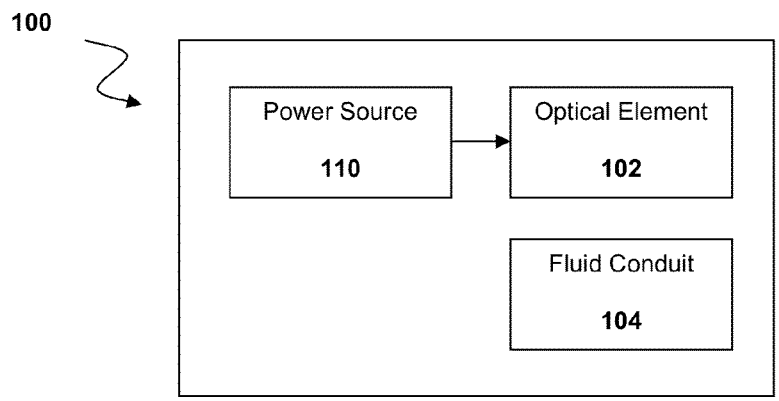
FIG. 1A depicts a block diagram of a tubing set system according to an embodiment.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

Embodiments relate to an illuminated medical tubing set that provides visual indications of characteristics relating to the type and operating status of the tubing. In embodiments, single and dual lumen tubing can be used. In one dual lumen embodiment, one lumen is used is used as the lighted channel, and the other lumen is used to transport the drug or fluid. In another embodiment, an inner lumen is nested within an outer lumen, whereby either the inner lumen is used as the lighted channel and the outer lumen is used as the fluid conduit, or the outer lumen is used as the lighted channel and the inner lumen is used as the fluid conduit. The inside surface of a single channel of tubing is optically coated with a side-emitting material in another embodiment. In such an embodiment, a single channel is utilized as the conduit for both the transportation of the fluid and the transportation of the light or color. In another embodiment, the outside surface of a single channel of tubing is optically coated with a side-emitting material. Both the outside and inside surfaces of a single channel of tubing are optically coated with a side-emitting material in another embodiment. In yet another embodiment, a segment of EL wire is coupled to medical tubing such that, when current is passed through the EL wire, the wire and consequently, the adjoining tubing, are illuminated. Light-emitting diodes (LEDs) are positioned at opposite ends of or along the tubing in order to illuminate the length of tubing in another embodiment. Various other combinations and configurations of these and other components can be implemented in other embodiments.

Figure 1B:
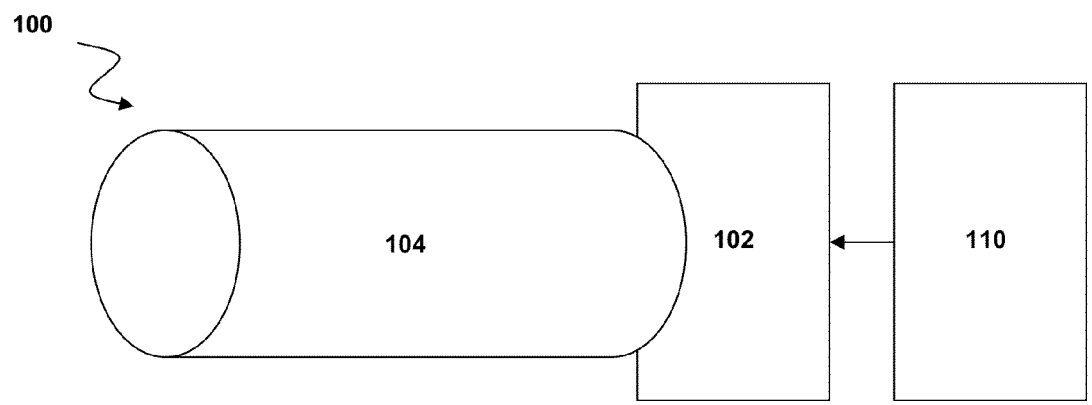
FIG. 1B depicts a block diagram of a tubing set system according to an embodiment.
Figure 1C:
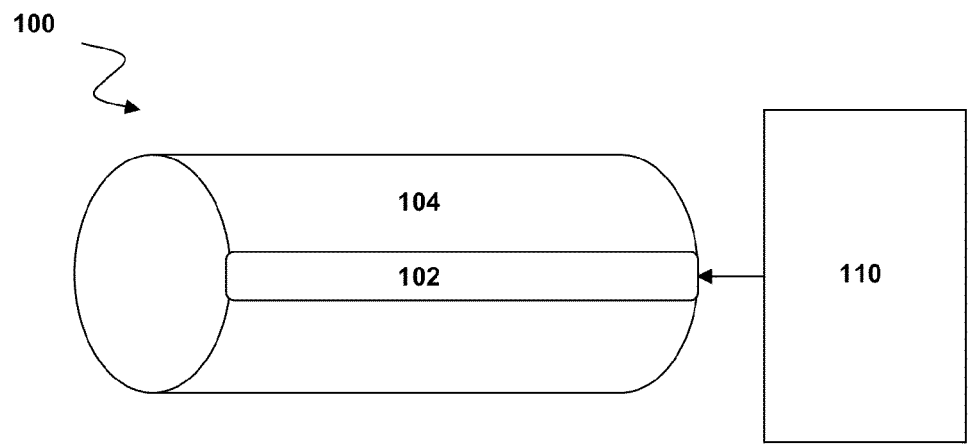
FIG. 1C depicts a block diagram of a tubing set system according to an embodiment.
Figure 2:
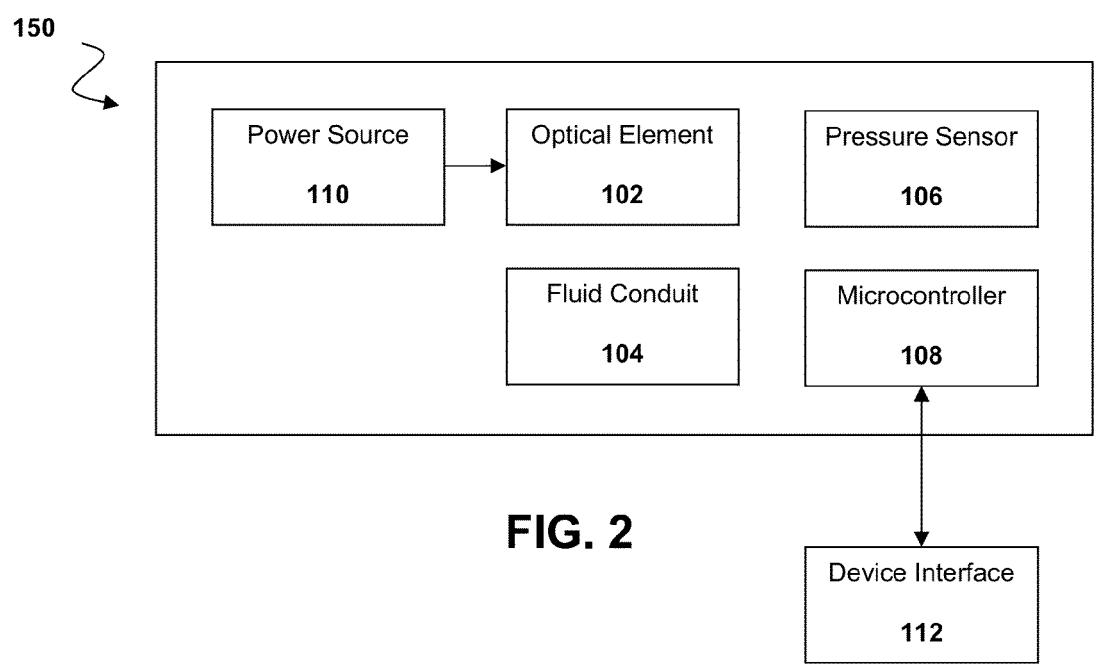
FIG. 2 depicts a block diagram of a tubing set system according to an embodiment.

Referring generally to FIGS. 1A-1C, block diagrams of an illuminated tubing set system 100 are depicted, according to embodiments. Embodiments of illuminated tubing set system 100 generally comprise an optical element 102, a fluid conduit 104, and a power source 110. Example embodiments of illuminated tubing set 100 are described below. In general, power source 110 interfaces with optical element 102, and optical element 102 is configured to illuminate tubing set 100. Optionally, and as depicted in FIG. 2, in another embodiment, illuminated tubing set 150 can further comprise a pressure sensor 106 and a microcontroller 108. Additional sensors, such as to monitor other characteristics of the tubing, fluid, or surrounding environment, can also be included in other embodiments. For example, an occlusion sensor, temperature sensor, flow sensor, liquid density sensor, air bubble sensor, salinity sensor, pH sensor, dissolved oxygen sensor, conductivity sensor, electrolyte sensor, or any combination thereof, can be included in embodiments.

In another embodiment (not depicted), illuminated tubing set 150 can comprise optical element 102, fluid conduit 104, power source 110, and one or more sensors, without microcontroller 108. Further, one or more sensors can comprise, for example, a pressure sensor, occlusion sensor, temperature sensor, flow sensor, liquid density sensor, air bubble sensor, salinity sensor, pH sensor, dissolved oxygen sensor, conductivity sensor, electrolyte sensor, or any combination thereof. In embodiments without microcontroller 108, an integrated circuit (IC) or other generic chip can optionally be included. The IC is configured to provide information to device interface 112 via an electronic signal. In an embodiment, the IC can provide identifying information such as part number, lot number, or expiration date, for example.

Referring again to FIG. 1A, optical element 102 provides an illuminated visual indicator for tubing set 100. In embodiments, optical element 102 runs continuously and lengthwise for the length of tubing set 100, as depicted, for example, in FIG. 1C. The visual indicator in embodiments is therefore equally as bright and illuminated at the midpoint of tubing set 100 as it is at the interface to power source 110. For example, in an embodiment, optical element 102 comprises a side-emitting optical coating running the length of tubing set 100 and a light-generating element, such as a laser or other concentrated light source. In such an embodiment, power source 110 powers the light-generating element, which directs light along the side-emitting optical coating. Light is reflected along the length of tubing set 100 to illuminate tubing set 100. The optical coating can be an adhesive acrylate-based cladding solution, or any other coating appropriate for a plastic or silicone substrate. In an embodiment, the optical path for optical element 102 is co-extruded with fluid conduit 104 at the time of manufacture. In another embodiment, optical element 102 comprises an illuminated EL wire running the length of tubing set 100. In another embodiment, optical element 102 is positioned at discrete points along tubing set 100, for example, and comprises one or more illuminable LEDs, such as multi-color LEDs. In such an embodiment, power source 110 powers discrete lights or indicator elements at certain illumination points, for example, at the interface point with power source 110, as depicted, for example, in FIG. 1B. Both a greater number and lesser number of illumination points are considered. For example, optical element 102 points can be at the interface with power source 110 and near the patient contact site. In another example, illumination points can be at the interface point with power source 110, at the midpoint of tubing set 100, and near the infusion or patient contact site.

Optical element 102 can be configured to provide white light or colored light, or to provide no light, or to selectively alternate between one or more lighted and/or non-lighted settings. Further, optical element 102 can provide varying degrees of brightness. In certain situations, like when a patient's room is darkened—at night, for example—the brightness of optical element 102 can be reduced. The reduced intensity light of optical element 102 is still easily visible in the darkened ambient lighting, yet not bright enough to disturb the patient. Conversely, when the ambient lighting is brightened—during the day, for example—the brightness of optical element 102 can be increased to increase the ease of visibility of tubing set 100. Additionally, optical element 102 can be configured to provide flashing or patterned light. Examples of such flashing or patterned light are given below. Additional optical elements, like a chemiluminescent fluid, can also be included in other embodiments.

Fluid conduit 104 is used to transmit fluid in a critical care environment. For example, fluid conduit 104 can transmit medication from an infusion pump to a patient. Alternatively, fluid conduit 104 can provide the conveyance for removing fluid from a patient. Fluid conduit 104 generally comprises a cylinder with a diameter wide enough for fluid to flow appropriately for the medical application. Thus, fluid conduit 104 can have diameters of different sizes in various embodiments. For example, fluid conduit 104 having diameters of about 0.015 inches to about 3.0 inches are contemplated. Other diameters are also considered. Fluid conduit 104 is typically made of a flexible silicon plastic appropriate for a medical environment, such that it is odorless, tasteless, and inert. Further, fluid conduit 104 is nonreactive to body tissues and fluids and can withstand repeated sterilizations. Other appropriate materials are also considered, like polyvinyl chloride or any other appropriate thermoplastic polymer. Fluid conduit 104 can also be of varying lengths, depending on the medical application. In embodiments, fluid conduit 104 can provide the conveyance for both the medical fluid as well as the housing for optical element 102. Typically, fluid conduit 104 is clear or transparent so that the fluid flowing throughout fluid conduit 104 is visible through the walls of the cylinder. In other embodiments, however, fluid conduit 104 can be partially or fully translucent or opaque.

Power source 110 provides a source of the power for optical element 102. In embodiments, power source 110 can be integrated into the medical device to which tubing set 100 interfaces. In other embodiments, power source 110 can be integrated within the body of fluid conduit 104 or another portion of tubing set 100 itself. Power source 110 generates or conveys the power required of the particular embodiment of optical element 102. For example, power source 110 can be a battery. In another example, power source 110 is an electrical connection to the power source of the medical device.

In an embodiment, for example one in which optical element 102 comprises a light-generating element and a side-emitting optical coating from which light can reflect, power source 110 is a battery that powers the light-generating element. A beam of focused light is directed by the light-generating element appropriately along the sides of the conduit of the optical coating to illuminate tubing set 100. In another embodiment, power source 110 comprises a source of alternating current, where optical element 102 comprises, for example, a length of EL wire. The alternating current is applied to the EL wire to illuminate the wire, the conduit housing optical element 102 and thus, tubing set 100. In another embodiment, power source 110 includes a voltage source designed to power an LED, where optical element 102 comprises an LED. The above-described power sources are provided for example only and are not intended to be limiting for power source 110. Any appropriate power source can be used. For example, in embodiments, direct current, battery, linear regulated, switched mode power sources, or any other useful power source can be utilized.

In embodiments, and referring to FIG. 2, tubing set 150 can further comprise pressure sensor 106. Pressure sensor 106 is used to monitor the pressure of the fluid within fluid conduit 104. By measuring the pressure, emergency or alertable situations can be detected for the fluid flow within fluid conduit 104. In embodiments (not depicted), tubing set can comprise any useful sensor, for example, occlusion sensor, temperature sensor, flow sensor, liquid density sensor, air bubble sensor, salinity sensor, pH sensor, dissolved oxygen sensor, conductivity sensor, electrolyte sensor, or any combination thereof. Similar to the above-described monitoring of pressure sensor 106, any of the aforementioned sensors can monitor fluid conduit 104 and subsequently relay emergency or alertable situations, depending on the specifics of the respective sensor.

In embodiments, tubing set 150 can further comprise microcontroller 108. Microcontroller 108 is used to capture the pressure sensed by pressure sensor 106. Algorithms regarding pressure changes can be programmed into microcontroller 108. In an example, if the measured pressure is outside of a particular boundary or the measured delta is outside limits placed on a previously-measured acceptable value, an alert situation may be present. Further, microcontroller 108 provides an interface to control power source 110. In this way, various colored lights or flashing patterns can be implemented. In the alert situation described above, microcontroller can signal to power source 110 that a non-standard operating status should be indicated. Myriad algorithms can be implemented, given this framework, to alert and provide status of the operation of the tubing set. Examples are given herein below.

Device interface 112 can provide an interface for programming basic operation, alarm indicators (including appropriate limits), colors, and other operating parameters into microcontroller 108. In an embodiment, device interface 112 is implemented as part of a medical device, such as an infusion pump. In another embodiment, device interface 112 is implemented as a stand-alone component of tubing set 150.

Device interface 112 can be configured to provide standardized operating parameters to microcontroller 108. Standardized profiles or configurations having standardized operation, alarm indications, colors, and other operating parameters can be implemented for each medical device for a particular hospital site. Each type of medical device can have a specific profile with operating parameters unique to that device. Similarly, a specific profile can be developed for each set of tubing implemented having a specific sensor or set of sensors. Device interface 112 can be configured to install these profiles, and thereby adjust the operating settings, prior to the use of the medical device. For example, a particular hospital could standardize all occlusion pressure alarms to flash tubing set 150 with the color red. Such a configuration allows for uniformity across an entire hospital site, thus further easing burden on medical professionals and further providing value with tubing set 150 use. At that particular hospital site, all medical professionals would know that a flashing red tubing set indicates an occlusion problem.

Figure 3:
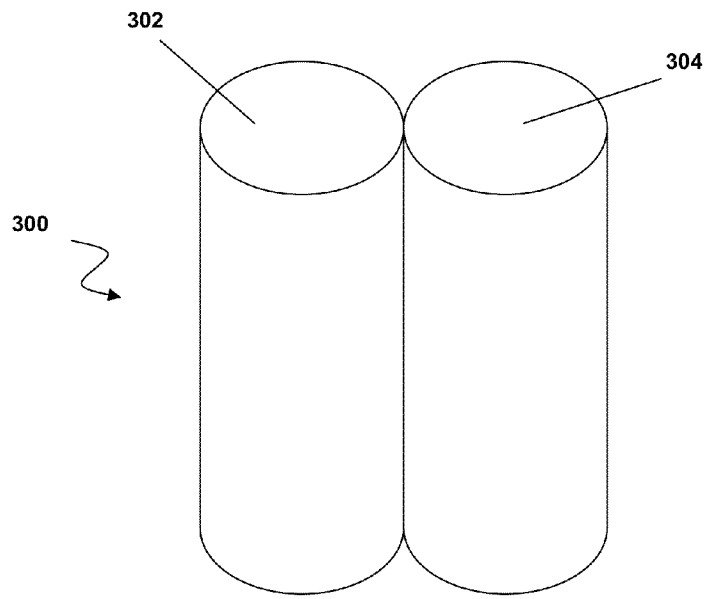
FIG. 3 is a perspective view of a dual lumen tubing set according to an embodiment.

Referring to FIG. 3, an embodiment of a dual lumen tubing set 300 is depicted. Dual lumen tubing set 300 generally comprises an optical interface 302 and a fluid conduit 304. Optical interface 302 can be, for example as described above with respect to optical interface 102, a fiber optic channel, a length of EL wire extending throughout the channel, or a series of LEDs placed along the channel, among others. Optical interface 302 and fluid conduit 304 are immediately adjacent each other in one embodiment so that when optical interface 302 is illuminated, fluid conduit 304 is also illuminated.

Figure 4:
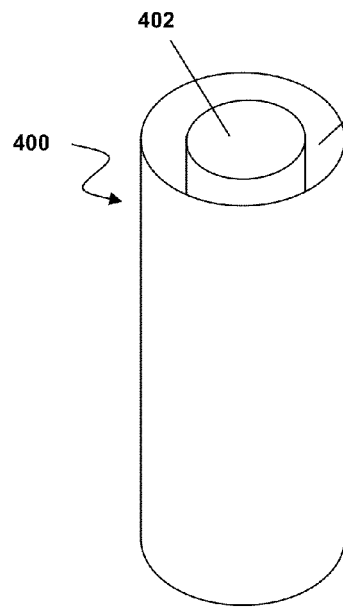
FIG. 4 is a perspective view of a tubing set utilizing an inner lumen and an outer lumen according to an embodiment.

Referring to FIG. 4, an embodiment of a dual lumen tubing set 400 is depicted. Dual lumen tubing set 400 generally comprises an inner lumen 402 and an outer lumen 404. Inner lumen 402 is nested within outer lumen 404 such that inner lumen 402 is completely enclosed by outer lumen 404. In an embodiment, inner lumen 402 provides the fluid conduit and outer lumen 404 provides the housing for the optical interface for dual lumen tubing set 400. When illuminated using appropriately clear or transparent lumens, the optical element in outer lumen 404 illuminates inner lumen 402 and the fluid flowing throughout. In another embodiment, inner lumen 402 provides the housing for the optical interface and outer lumen 404 provides the fluid conduit for dual lumen tubing set 400. When illuminated, the optical element in inner lumen 402 illuminates outer lumen 404 and the fluid flowing throughout. In embodiments, the optical interface can be, as described above with respect to optical interface 102, a fiber optic channel, a length of EL wire extending throughout the channel, or a series of LEDs placed along the channel. In other nested embodiments (not depicted), additional lumens can extend throughout the outermost lumen, with multiple fluids flowing throughout, depending on the medical application. Whichever lumen is chosen as the fluid conduit can illuminate the remaining fluid conduit lumens.

Figure 5:
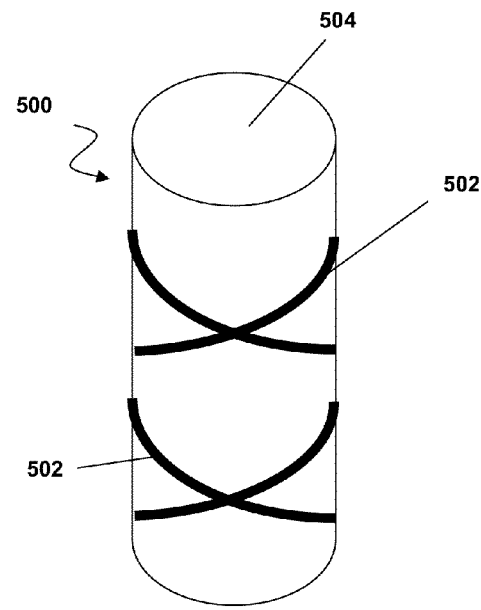
FIG. 5 is a perspective view of a tubing set utilizing an electroluminescent (EL) wire according to an embodiment.
Figure 6:
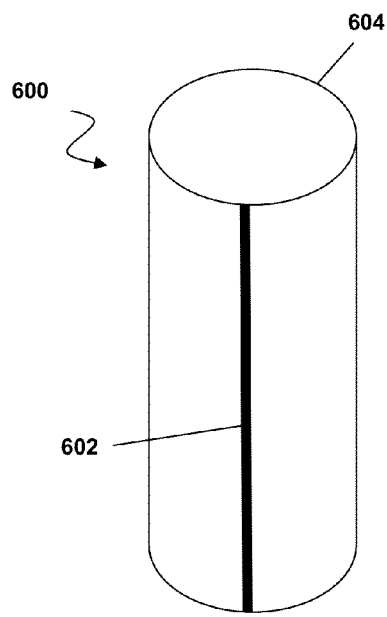
FIG. 6 is a perspective view of a tubing set utilizing an EL wire according to an embodiment.

Referring to FIG. 5, an embodiment of tubing set 500 using an EL wire is depicted. Tubing set 500 generally comprises an optical element 502 and a fluid conduit 504. In such an embodiment, optical element 502 is a length of EL wire. Optical element 502 is encircled around and coupled to the outer wall of fluid conduit 504 in a crisscrossing pattern. Similarly, referring to FIG. 6, another embodiment of a tubing set 600 using EL wire is depicted. Tubing set 600 generally comprises an optical element 602 and a fluid conduit 604. Again, in such an embodiment, optical element 602 is a length of EL wire. Optical element 602 is coupled to the outer wall of fluid conduit 604 along one side of the outer wall. When optical element 502 or optical element 602 are illuminated, respective fluid conduits 504 or 604 are similarly illuminated. In operation, to illuminate optical element 502 or 602 and thus fluid conduit 504 or 604, an alternating current is applied to one end of the EL wire of optical element 502 or 602.

Figure 7:
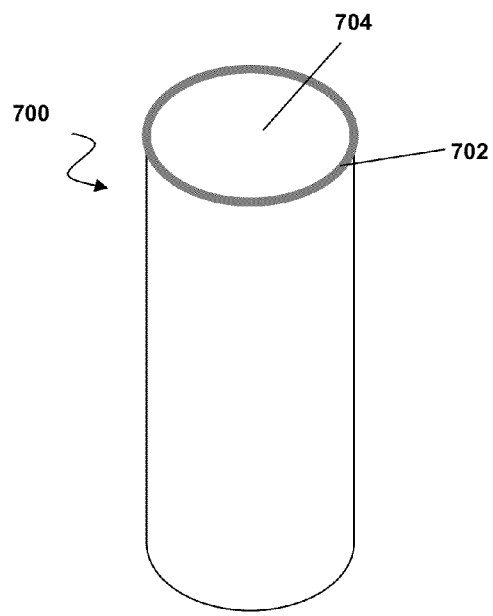
FIG. 7 is a perspective view of a tubing set utilizing an interior optical coating according to an embodiment.

Referring to FIG. 7, an embodiment of tubing set 700 comprising a side-emitting optical coating is depicted. Tubing set 700 generally comprises an optical element 702 and a fluid conduit 704. In such an embodiment, optical element 702 comprises a side-emitting optical coating and a light-generating element. The side-emitting coating of optical element 702 is coated along the inside walls of fluid conduit 704. The combination of the light-generating element and the optical coating, when light is directed by the light-generating element along the coated walls of fluid conduit 704 provides an illuminated fluid conduit 704. Tubing set 700 therefore has a single conduit; fluid conduit 704 provides the conveyance for both the medical fluid as well as the housing for the optical element.

Figure 8A:
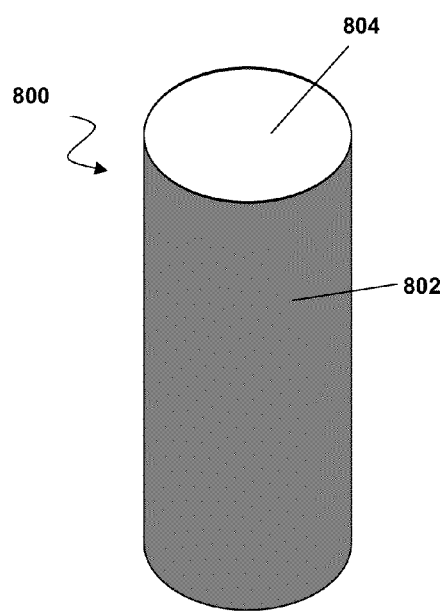
FIG. 8A is a perspective view of a tubing set utilizing an exterior optical coating according to an embodiment.

Similarly, referring to FIG. 8A, an embodiment of tubing set 800 also comprising an optical coating is depicted. Tubing set 800 generally comprises an optical element 802 and a fluid conduit 804. Similar to tubing set 700, optical element 802 comprises a side-emitting optical coating and a light-generating element. However, unlike tubing set 700, tubing set 800 has the optical coating along the outer wall of fluid conduit 804.

In operation, to illuminate fluid conduit 704 or 804, a beam of focused light is directed appropriately at one end of fluid conduit 704 or 804 by the light-generating element of optical element 702 or 802, respectively, so that the light reflects along the coated sides of fluid conduit 704 or 804, respectively.

Figure 8B:
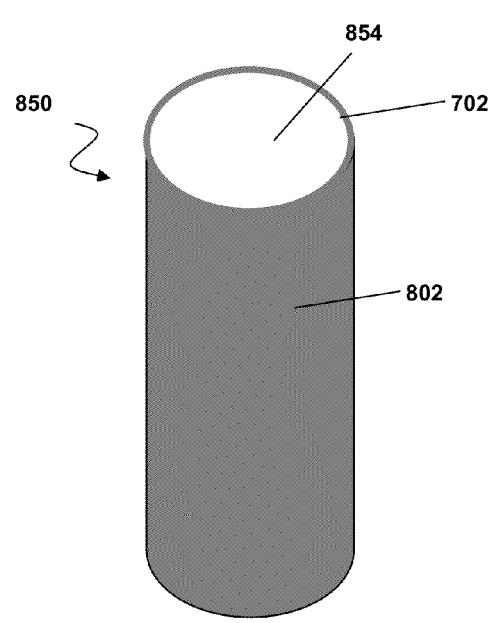
FIG. 8B is a perspective view of a tubing set utilizing both an interior optical coating and an exterior optical coating according to an embodiment.

Referring to FIG. 8B, an embodiment of tubing set 850 also comprising an optical coating is depicted. Tubing set 850 is a combination of tubing set 700 and tubing set 800. Tubing set 850 generally comprises an inside optical element 702 and an outside optical element 802, both optical elements 702 and 802 comprising a coating of side-emitting material such that there is optical coating on both the interior and exterior of the tubing wall, and a fluid conduit 854. In tubing set 850, the tube wall itself comprises the optical path.

In operation, to illuminate fluid conduit 854, a beam of focused light is directed appropriately within the wall of fluid conduit 854 by the light-generating element of optical element 702 or 802, respectively, so that the light reflects within the coated sides of fluid conduit 854. The combination of the light-generating element and the two optical coatings, when light is directed by the light-generating element within the wall of fluid conduit 854 provides an illuminated fluid conduit 854.

Figure 9:
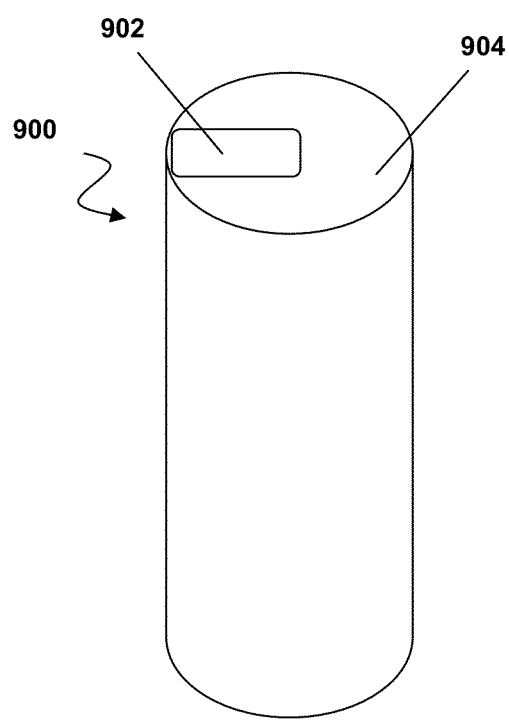
FIG. 9 is a perspective view of a tubing set utilizing LEDs according to an embodiment.

Referring to FIG. 9, an embodiment of tubing set 900 having one or more LEDs is depicted. Tubing set 900 generally comprises an optical element 902 and a fluid conduit 904. In such an embodiment, optical element 902 comprises at least one LED. As depicted, optical element 902 is positioned near an opening of fluid conduit 904, though other positionings, configurations, and arrangements are possible in other embodiments. As appropriate, additional optical elements 902 can be positioned along fluid conduit 904 to provide consistent illumination of fluid conduit 904 when optical elements 902 are illuminated. In operation, to illuminate optical element 902, a voltage is applied to the LED to thereby illuminate the LED and fluid conduit 904.

Figure 10:
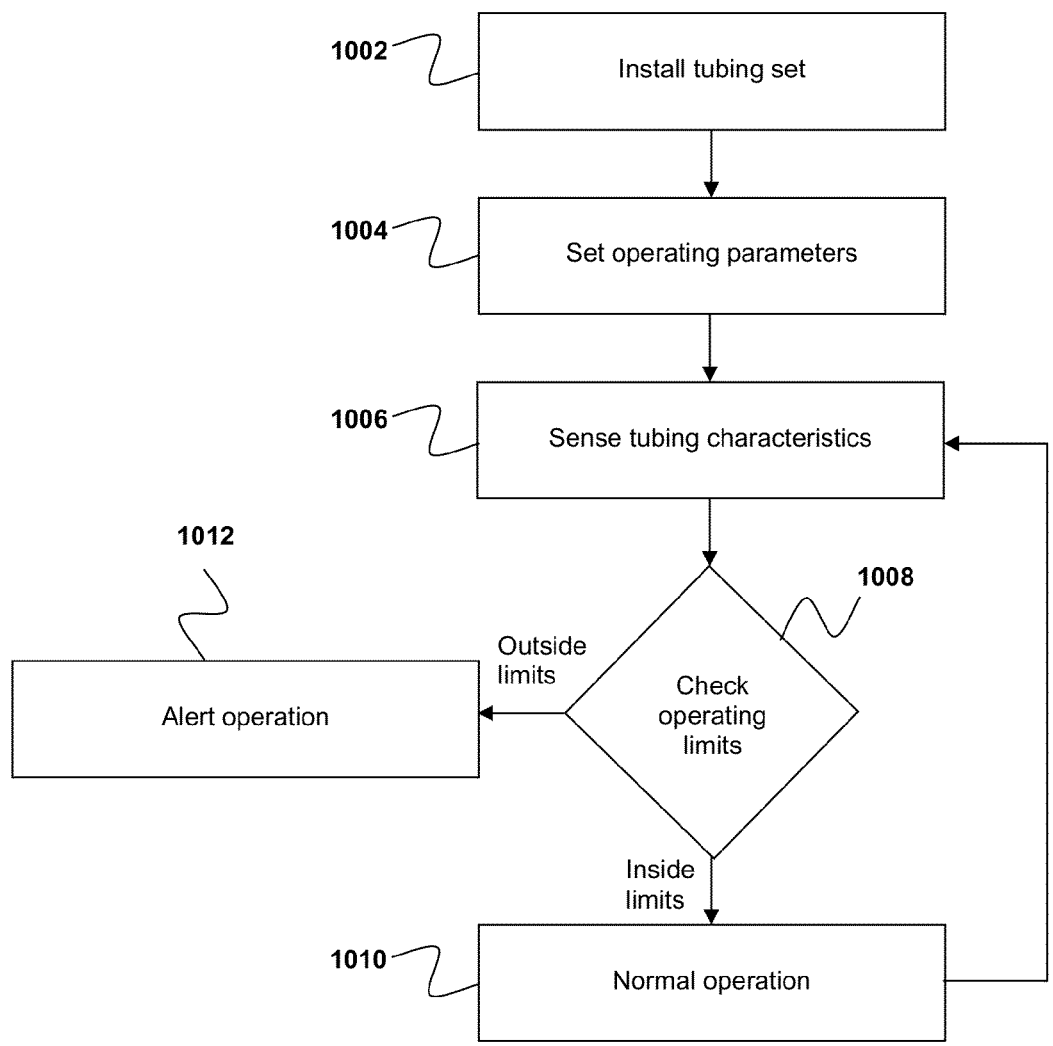
FIG. 10 is a flowchart of the operation of a tubing set according to an embodiment.

In operation generally, referring to FIG. 10, a tubing set is installed at 1002. Depending on the embodiment and application, installation can be any variation of securely coupling one end of the tubing set to a medical device and the opposite end to a patient, or as a drain from a patient to a waste-capturing device. Fluid conduit 104 is appropriately coupled to the fluid source. Further, optical element 102 and power source 110 are appropriately coupled together if required. For example, one installation can be connecting an infusion pump to a patient at an infusion site. The infusion pump can have an integrated power source 110 that is operably couplable to the optical element 102 of the tubing itself. Another installation can be connecting a feeding device to a patient at a feeding site where the tubing itself contains the power source 110, not the feeding device. Upon correct installation, the tubing set can illuminate or flash a known pattern or sequence to indicate correct installation.

At 1004, operating parameters are set. The color of tube, illumination intensity, and alarm limits for the various coupled sensors, and other operating parameters are programmed into microcontroller 108 via device interface 112. In some embodiments, the operating parameters are set automatically upon installation of the tubing set. For example, because of the standardization of colors and patterns in the medical industry, any tubing set connected to a specific device requiring a standard color or pattern can automatically be programmed by the device via device interface 112 to set microcontroller 108 with the standardized illumination, standard limits, and standard intensity for the application, without any additional human intervention. If the medical professional desires a different color scheme limits, or intensity, device interface 112, which can reside on a medical device, or as a separate interface, can be utilized to program microcontroller 108.

At 1006, an initial set of tubing characteristics are sensed. If pressure sensor 106 is present in the tubing set embodiment, as depicted in FIG. 2, the pressure of the tube is sensed. Further, or alternatively, any additional sensors, as described above, are activated to capture their respective sensor indications. At 1008, a check of operating limits is conducted. The decision point at 1008 is utilized to ensure that operation of the tube is within the set limits. This type of limit or boundary check is conducted for all attached sensors, or if desired, fewer than all attached sensors. If, for example, the pressure sensed by pressure sensor 106 is inside of expected limits, normal operation results at 1010. Normal operation 1010 can include a solid illumination at the desired programmed light intensity, or no illumination, if desired. If, however, the pressure sensed by pressure sensor 106 is outside of expected limits, alert operation results at 1012. Alert operation 1012 can include a flashing or patterned illumination to indicate some sort of problem with the tubing set. For example, a quicker flash might indicate a pressure or occlusion problem, whereas a slower flash might indicate a temperature problem. In another example, a pattern of three quick flashes followed by a pause of no illumination might indicate an improperly connected tubing set. In yet another example, a short flash followed by a long flash might indicate a microcontroller 108 fault. Any number of flashing or patterned flashes can be implemented to indicate status. Further, any attached medical device can utilize the illumination capability of the tubing set to indicate status for the medical device by operation via device interface 112.

In either the case of normal operation 1010 or alert operation 1012, power source 110 interfaces with optical element 102 to illuminate optical element 102 and the tubing set. When the tubing set is in normal operation, the recursive loop from normal operation at 1010 back to sense tubing characteristics at 1006 can be conducted in real time, or upon expiration of a standard or programmed wait period. Further, in operation, any of the operating parameters can be adjusted while the tubing set is in use.

Various embodiments of systems, devices and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. A method of operating a medical tubing set, with at least one of (i) the medical tubing set, or (ii) a combination of the medical tubing set and a medical device, comprising an optical element, the method comprising:
    installing the medical tubing set in the medical device at as first end and in a patient at a second end;
    setting at least one operating parameter of the medical tubing set;
    sensing at least one characteristic of the medical tubing set;
    comparing the at least one sensed characteristic against the at least one operating parameter; and
    illuminating the medical tubing set with the optical element based on at least the comparison of the at least one sensed characteristic and the at least one operating parameter.

2. The method of claim 1, wherein setting at least one operating parameter further comprises setting an illumination color.

3. The method of claim 1, wherein setting at least one operating parameter further comprises setting a pressure upper limit and a pressure lower limit.

4. The method of claim 1, wherein illuminating the tubing set further comprises intermittently illuminating the tubing set to create a flashing effect when the at least one sensed characteristic is outside of an operating range of the at least one characteristic set by the at least one operating parameter.

5. The method of claim 1, wherein illuminating the tubing set further comprises continuously illuminating the tubing set.

6. The method of claim 1, wherein setting at least one operating parameter is done automatically upon installation of the medical tubing set in the medical device.

7. The method of claim 1, wherein illuminating the tubing set further comprises applying a concentrated beam of light to a conduit having walls coated in a fiber optic coating.

8. The method of claim 1, wherein illuminating the tubing set further comprises applying a voltage to a light-emitting diode.

9. The method of claim 1, wherein illuminating the tubing set further comprises applying an alternating current to an electroluminescent wire.

* * * * *